United States Patent [19]

Marker et al.

[11] Patent Number: 5,750,800
[45] Date of Patent: May 12, 1998

[54] PROCESS FOR PRODUCING DIISOPROPYL ETHER FROM PROPANE

[75] Inventors: Terry L. Marker, Warrenville; Brian S. Muldoon, Willowbrook; Bryan K. Glover, Algonquin; Bipin V. Vora, Darien, all of Ill.

[73] Assignee: UOP, Des Plaines, Ill.

[21] Appl. No.: 556,117

[22] Filed: Nov. 9, 1995

[51] Int. Cl.$^6$ .................................................. C07C 41/00
[52] U.S. Cl. ........................ 568/678; 568/697; 568/627
[58] Field of Search .................................. 568/697, 698, 568/699

[56] References Cited

U.S. PATENT DOCUMENTS

| | | | |
|---|---|---|---|
| 3,907,921 | 9/1975 | Winter, III | 260/683.3 |
| 4,393,250 | 7/1983 | Gottlieb et al. | 568/697 |
| 4,806,695 | 2/1989 | Vora et al. | 568/697 |
| 4,816,607 | 3/1989 | Vora et al. | 568/697 |
| 4,868,342 | 9/1989 | Verson | 568/697 |
| 5,008,467 | 4/1991 | Vora et al. | 568/697 |
| 5,087,792 | 2/1992 | Cottrell et al. | 585/661 |
| 5,105,024 | 4/1992 | McKay et al. | 568/697 |
| 5,237,115 | 8/1993 | Makovec et al. | 585/314 |
| 5,313,004 | 5/1994 | Harandi et al. | 568/697 |
| 5,321,192 | 6/1994 | Cottrell et al. | 585/659 |
| 5,324,866 | 6/1994 | Marker et al. | 568/697 |
| 5,371,301 | 12/1994 | Marker et al. | 568/694 |
| 5,406,011 | 4/1995 | Radcliffe et al. | 585/254 |

FOREIGN PATENT DOCUMENTS

0382956B1  8/1994  European Pat. Off. .

*Primary Examiner*—Marianne M. Cintins
*Assistant Examiner*—Dwayne C. Jones
*Attorney, Agent, or Firm*—Thomas K. McBride; Eugene I. Snyder; Maryann Maas

[57] ABSTRACT

An integrated process to produce diisopropyl ether from propane has been developed. In a first reaction zone the propane in a feedstock, after any hydrocarbons containing four or more carbon atoms are removed from the feedstock via fractionation, is dehydrogenated in the presence of a dehydrogenation catalyst to form propylene. After removing hydrogen, the propane and propylene mixture generated in the first reaction zone is separated into a propane enriched stream and a propylene enriched stream where the propylene enriched stream contains at least 65 mass % propylene. The propane enriched stream is recycled to the feedstock fractionation unit, and the propylene of the propylene enriched stream is reacted with water in a second reaction zone in the presence of an acidic catalyst to form isopropyl alcohol which is concurrently reacted with propylene to produce diisopropyl ether. A portion of the second reaction zone effluent is recycled to the second reaction zone, and the remainder may be collected or further separated to provide a high purity diisopropyl ether product. A variant to produce high purity propylene as well as diisopropyl ether is also discussed.

11 Claims, 2 Drawing Sheets

PROCESS FOR PRODUCING DIISOPROPYL ETHER FROM PROPANE

BACKGROUND OF THE INVENTION

As tetraethyl lead is phased out, oxygenates have become more important in the petroleum refining industry as a source of gasoline octane boosters. The most common oxygenates for this purpose are the dialkyl ethers, especially those in the $C_5$ to $C_8$ range. One example of such a dialkyl ether is diisopropyl ether which is in the boiling range of gasoline and has a high blending octane number of 105 and a blending Reid vapor pressure of 5. Diisopropyl ether is typically prepared from propylene by two sequential reactions: (1) where propylene is first hydrated to isopropyl alcohol followed by reaction of the alcohol with the olefin, or (2) by a single bimolecular dehydration reaction of the alcohol (Williamson synthesis). The propylene may be prepared from the dehydrogenation reaction of propane. Applicants have discovered a process that integrates the propane dehydrogenation process with the diisopropyl ether production process so that diisopropyl ether is ultimately produced from propane. The integration allows for significant reduction in capital investment since several units may be eliminated or reduced in size as compared to traditional individual flowschemes.

The dehydrogenation of propane to form propylene is well known in the art as shown by U.S. Pat. Nos. 5,321,192, 5,406,011 and U.S. Pat. No. 5,087,792. Similarly, the preparation of diisopropyl ether from propylene and water is well known and numerous processes exist in the art such as U.S. Pat. Nos. 5,324,866 and 5,371,301. Dehydrogenation of a paraffin to form an olefin and subsequent etherification of the olefin with an alcohol containing feedstock to form an ether is also known in the art, especially in the case were the target product is methyl tertiary butyl ether; see E.P. 382 956 B1,U.S. Pat. Nos. 5,313,004, 4,806,695, 5,008,467, and 4,816,607. In the present invention, however, the need to provide an independent alcohol containing feedstock is eliminated since the alcohol needed to form diisopropyl ether is formed in the process.

Other processes combine dehydrogenation with etherification or alkylation, see U.S. Pat. Nos. 5,105,024 and 4,868,342, respectively, but in these patents, if propylene is produced in the dehydrogenation, it is separated as a product and not passed downstream for further processing. In one patent, U.S. Pat. No. 4,393,250, the propylene product of a dehydrogenation process is hydrated to form isopropyl alcohol which is then reacted with the isobutylene product of the same dehydrogenation process to form isopropyl tert-butyl ether. U.S. Pat. No. 5,237,115 discloses another process where the olefins produced by dehydrogenation are hydroisomerized prior to etherification.

Applicants are the first to realize that a propane dehydrogenation process to form propylene can be economically and efficiently integrated with a diisopropyl ether production process. Specifically, 1) the integration eliminates the need for a selective hydrogenation unit since diolefins generated in the dehydrogenation zone do not need to be converted to olefins and instead may be passed to the diisopropyl ether reaction zone, 2) the integration reduces the need of two propane-propylene splitters to only one propane-propylene splitter and furthermore decreases the size and cost of the one required propane-propylene splitter, 3) in the preferred embodiment, the integration eliminates the need for a de-ethanizer, and 4) due to the nature of the reactions, eliminates the need for an independent alcohol feedstock.

SUMMARY OF THE INVENTION

The purpose of this invention is to provide an integrated process to produce diisopropyl ether from propane. In a first reaction zone, the propane in a feedstock, after any hydrocarbons containing four or more carbon atoms are removed from the feedstock via fractionation, is dehydrogenated in the presence of a dehydrogenation catalyst to form propylene. After removing hydrogen, the propane and propylene mixture generated in the first reaction zone is separated into a propane enriched stream and a propylene enriched stream where the propylene enriched stream contains at least 65 mass % propylene. The propane enriched stream is recycled to the feedstock fractionation unit, and the propylene of the propylene enriched stream is reacted with water in a second reaction zone in the presence of an acidic catalyst to form isopropyl alcohol which is concurrently reacted with propylene to produce diisopropyl ether. A portion of the second reaction zone effluent is recycled to the second reaction zone, and the remainder may be collected or further separated to provide a high purity diisopropyl ether product.

A more specific embodiment of the invention is one where high purity propylene, in addition to diisopropyl ether, is collected as a product. In this embodiment, hydrogen is removed from the first reaction zone effluent, and any methane, ethane, and ethylene are also removed. The light ends depleted propane and propylene mixture is then separated as above into a propane enriched stream and a propylene enriched stream where the propylene enriched stream contains at least 65 mass % propylene. However, in this embodiment the propylene enriched stream is divided into two portions with the first portion being passed to a finishing column to remove additional propane and afford a high purity propylene stream containing at least 99.5 mass % propylene and a low purity propylene stream. The high purity propylene stream may be collected as product and the low purity propylene stream is recycled to the propane-propylene splitter or passed to the diisopropyl ether reaction zone. The second portion of the propylene enriched stream from the propane-propylene splitter is processed as above to produce diisopropyl ether.

Figure 1:
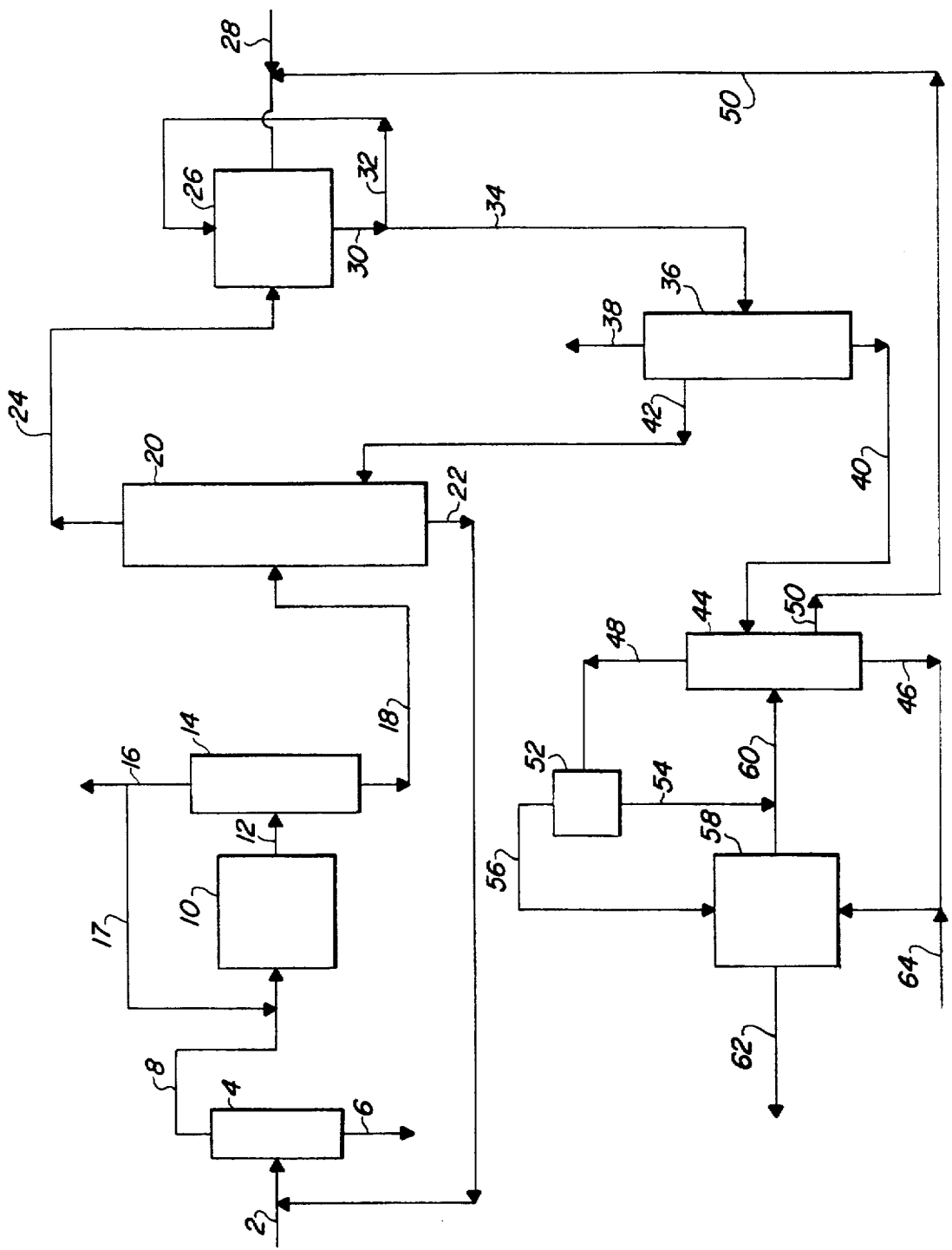
FIG. 1 is a schematic representation of the preferred embodiment of the invention.

The drawings have been simplified by the deletion of a large number of pieces of apparatus customarily employed in processes of this nature which are not specifically required to illustrate the performance of the subject invention.

DETAILED DESCRIPTION OF THE INVENTION

The invention integrates two known processes, a paraffin dehydrogenation process and a diisopropyl ether production process, in a unique configuration so that diisopropyl ether is ultimately produced from propane. In general terms, the propane is first dehydrogenated to form propylene in a first reaction zone. The propylene is separated from unreacted propane and is reacted with water in a second reaction zone to form isopropyl alcohol. Concurrently, in the second reaction zone, the isopropyl alcohol is reacted with propylene to form diisopropyl ether which is collected. The integration of the two processes provides substantial capital cost savings due to reducing the number of units required in the overall invention as compared to the sum of the number of units required in two freestanding processes. Also, the size of an extremely expensive unit used in the freestanding dehydrogenation process is significantly reduced, thereby greatly decreasing the cost of the unit and hence the process.

The process of the invention begins with the fractionation of the paraffinic feedstock. Typically, the feedstock will contain mainly propane, usually 90 mass %, with a small amount of ethane and some hydrocarbons containing four or more carbon atoms. The feedstock is fractionated to remove those hydrocarbons containing four or more carbon atoms in order to facilitate high conversion from paraffin to olefin and lessen the deactivation of the dehydrogenation catalyst. The feedstock fractionation unit is operated at conditions sufficient to achieve a fractionated feedstock containing at least 95 mass % propane, preferably 97 mass % propane. The fractionated feedstock is substantially depleted, i.e., containing no more than 0.5 mass %, of hydrocarbons containing greater than three carbon atoms.

The fractionated feedstock is passed to the first reaction zone where dehydrogenation takes place. The catalyst used in the dehydrogenation reaction zone may be any suitable catalyst known in the art for such reactions. A typical example includes a catalyst with a platinum component, a Group IVA component, an alkali or alkaline earth component, a halogen component, and a porous carrier material. Dehydrogenation catalysts are well known in the art and therefore are not described in detail here. For reference, see U.S. Pat. Nos. 5,321,192, 5,406,011, 4,806, 695, and 4,868,342. Conditions in the dehydrogenation reaction zone generally include temperatures from about 400° C. to about 700° C., pressures of about 5 psia to about 150 psig, and liquid hourly space velocities of about 0.1 to about 100 $hr^1$. The pressure is maintained as low as practicable, consistent with equipment limitations, to maximize the chemical equilibrium advantages. The preferred pressure range is about atmospheric, or 14.7 psia, to about 100 psig. It is advantageous to maintain the pressure at slightly above atmospheric pressure to avoid operation in a vacuum which requires specific additional safety considerations and is more expensive. The exact dehydrogenation conditions may depend on a variety of factors including the composition of the fractionated feedstock, the activity of the selected catalyst, and the hydrocarbon conversion rate.

The dehydrogenation reaction zone typically contains two or more beds of catalyst and the contacting may be accomplished in a fixed catalyst bed mode, a moving catalyst bed mode, a fluidized catalyst bed mode, or in a batch type operation. The moving catalyst bed mode is preferred. A diluent, such as recycled hydrogen, may be admixed with the fractionated feedstock prior to or in the dehydrogenation reaction zone. Furthermore, water or a water precursor may be added to the reaction mixture.

The dehydrogenation reaction zone effluent contains mainly propane, propylene, hydrogen, and some methane, ethane and ethylene. The effluent is cooled and a hydrogen-rich vapor is separated from a hydrocarbon-rich liquid phase. A portion of the methane, ethane, and ethylene will separate into the hydrogen-rich vapor but the bulk will separate into the hydrocarbon-rich liquid phase. During the dehydrogenation reaction some diolefins such as propadiene and methyl acetylene may be formed. In a freestanding dehydrogenation process to produce propylene, the diolefin formation poses a problem to the propylene product purity. Therefore, typically the diolefins are converted to olefins by selective hydrogenation. Due to the integration of the dehydrogenation process with a diisopropyl ether production process in the present invention, however, the diolefins do not need to be converted to olefins since they will be reacted downstream to form additional high octane compounds, such as acetone, which are acceptable to have in the ultimate diisopropyl ether product stream. The integration of the two processes makes the deletion of a selective hydrogenation unit from the process flowscheme possible and results in a capital cost savings.

Also, in a freestanding dehydrogenation process to produce propylene, the propylene product is typically required to be of polymer grade or containing at least 99.5 mass % propylene. To achieve this purity, substantially all methane, ethane, and ethylene present in the dehydrogenation reaction zone effluent must be removed. A fractionation column, or de-ethanizer, is generally used to accomplish the removal. However, with the integration provided in the current invention, it is not necessary to remove the methane, ethane, and ethylene at this point. The ethylene will be reacted downstream to form isopropyl ethyl ether which itself is a desirable product, and the methane and ethane will be removed in a downstream fractionation zone, thereby eliminating the need for more than one fractionation column to remove light ends.

The unconverted propane is removed from the dehydrogenation reaction zone effluent by a propane-propylene splitter which is one or more fractionation columns working together to separate the effluent into a propane enriched portion and a propylene enriched portion. The separation of propane and propylene is difficult and the higher the desired purity of the propylene product, the more extensive and costly the propane-propylene splitter must be. Therefore, in a freestanding dehydrogenation process where polymer grade propylene is desired, the propane-propylene splitter is large and quite expensive. However, because of the integration of the present invention, a smaller and less costly propane-propylene splitter is all that is required. In the present invention, the propylene enriched stream from the propane-propylene splitter may contain as little as 65 mass %, preferably at least 75 mass %, propylene as opposed to the 99.5 mass % required for polymer grade propylene. The importance of this reduction in propylene purity from 99.5 mass % to as little as 65 mass % is exemplified in that the number of trays in the propane-propylene splitter may be reduced from about 200–230 trays to about 90–110 trays, thereby reducing the height of the unit from 215 feet to about 100 feet. This reduction translates into substantial cost savings. The propane enriched stream from the propane-propylene splitter is recycled to the feedstock fractionation unit, and the propylene enriched stream is passed to the diisopropyl ether reaction zone.

Water and the propylene of the propylene enriched stream are reacted in the diisopropyl ether reaction zone in the presence of an acidic ion exchange resin catalyst. The operating conditions of the reaction zone include pressures of about 100 to about 1500 psia, preferably from about 700 to about 1000 psia, and temperatures of about 130° C. to about 180° C., preferably from about 135° C. to about 165° C. It is common to slowly increase the operating temperature as the catalyst ages. Suitable water to olefin mole ratios generally include from about 0.1:1 to about 0.8:1, preferably about 0.5:1.

The acidic ion exchange resin catalysts may be any of those commonly used for a diisopropyl ether production process including sulfonated cation exchange resins such as sulfonated polystyrene resins and sulfonated styrene/ divinylbenzene co-polymers. An example of a suitable sulfonated styrene/divinylbenzene co-polymer catalyst is Amberlyst 36 sold by Rohm and Haas. These sulfonated cation exchange resins are common in the art and do not require discussion here. For reference, see U.S. Pat. No. 5,371,301, G.B. 1,176,620, and U.S. Pat. No. 4,182,914. Halogenated strong acid ion exchange resins such as those described in U.S. Pat. Nos. 4,705,808, 4,269,943, and 3,256,250 may also be used. Acidic zeolites such as those disclosed in U.S. Pat. Nos. 5,144,086, 4,857,664, 4,906,787, and 4,214,107 are also suitable.

As the propylene and water contact the catalyst, the hydration reaction takes place and isopropyl alcohol is formed. As the isopropyl alcohol and propylene contact the catalyst, the etherification reaction takes place and diisopropyl ether is formed. Bimolecular dehydration reaction of the isopropyl alcohol may also take place to form diisopropyl ether, but it is less preferred due to the increased consumption of isopropyl alcohol as compared to the etherification reaction of isopropyl alcohol and propylene. Any ethylene present would also react with isopropyl alcohol to form isopropyl ethyl ether.

A portion of the diisopropyl ether reaction zone effluent is recycled to the diisopropyl ether reaction zone and the remainder is passed to a light ends fractionation zone for removal of compounds such as methane, ethane, ethylene, propylene and propane. The light ends fractionation zone may be operated at a temperature of about 40° C. to about 185° C. and a pressure of about 325 psig. The lightest compounds such as methane, ethane, and ethylene are withdrawn as overhead. A sidecut containing propylene and propane is recycled to the propane-propylene splitter discussed earlier. The heavier compounds such as water, isopropyl alcohol, and diisopropyl ether are passed to a water-isopropyl alcohol-diisopropyl ether splitter column.

The water-isopropyl alcohol-diisopropyl ether splitter column is a fractionation column operating from about 65° C. to about 120° C. and from about 10 to about 20 psig that separates the heavier compounds into a diisopropyl ether-isopropyl alcohol-water azeotrope stream, the water into another stream, and an isopropyl alcohol-water azeotrope into a yet another stream. The water stream is passed to a water wash zone, discussed below, and the diisopropyl ether-isopropyl alcohol-water azeotrope stream is passed to a settler. The isopropyl alcohol-water azeotrope stream is recycled to the diisopropyl ether reaction zone without breaking the azeotrope In the settler, the diisopropyl ether-isopropyl alcohol-water azeotrope forms two phases, a diisopropyl ether enriched phase of about 95 mass % diisopropyl ether, about 1 mass % water, and about 4 mass % isopropyl alcohol, and a water enriched phase of about 94 mass % water, about 1 mass % diisopropyl ether, and about 5 mass % isopropyl alcohol. The water enriched phase is recycled either directly to the water-isopropyl alcohol-diisopropyl ether splitter or is combined with the isopropyl alcohol and water stream exiting the water wash zone; see below. The diisopropyl ether enriched phase is passed to a water wash zone.

The water wash zone is operated at from about 40° C. to about 66° C. and from about 10 to about 40 psig. The diisopropyl ether enriched phase and a water stream, which includes the water stream from the water-isopropyl alcohol-diisopropyl ether splitter, are introduced to the water wash zone in a ratio of about 1:5 to about 1:10 to form an isopropyl alcohol and water stream which is recycled to the water-isopropyl alcohol-diisopropyl ether splitter, and a diisopropyl ether stream, containing at least 96 mass % diisopropyl ether, which is collected as product.

A variant of the invention allows for the collection of polymer grade propylene as a product in addition to diisopropyl ether. In this variant, the feedstock is fractionated, the propane dehydrogenated, and the hydrogen removed from the dehydrogenation reaction zone effluent as discussed above. However, to achieve the desired purity of the propylene product, an additional fractionation column, or de-ethanizer, is necessary to remove substantially all the methane, ethane, and ethylene that might be present. The de-ethanizer is generally operated at conditions sufficient to achieve at least 99.5 mass % propylene purity in the ultimate propylene product. The de-ethanizer overhead containing methane, ethane, and ethylene is removed, and the de-ethanizer bottoms containing propane, propylene, and perhaps diolefins and hydrocarbons containing greater than four carbon atoms is passed to the propane-propylene splitter described earlier. The size of the propane-propylene splitter in this variant is the same as required for the preferred embodiment.

The propylene enriched stream from the propane-propylene splitter containing at least 65 mass % propylene is divided into two portions. The first portion is passed to a finishing column to remove additional propane thereby yielding the 99.5 mass % propylene product. If less than polymer grade propylene is desired, the operating conditions can be adjusted so that the desired purity is met, usually at least 90 mass % propylene is desired. The propane containing bottoms of the finishing column may still contain a significant amount of propylene, as long as the concentration of propylene in the propylene containing overhead meets the purity requirements. The propane containing bottoms may be recycled to the propane-propylene splitter or may be passed to the diisopropyl ether reaction zone, and the propylene containing overhead is collected as high purity propylene product. The second portion of the propylene enriched stream from the propane-propylene splitter is conducted to the diisopropyl ether reaction zone and is processed as discussed above to yield diisopropyl ether product.

Without intending any limitation of the scope of the present invention and as merely illustrative, the invention is explained below in specific terms as applied to a specific embodiment of the invention which is based on a design for a commercial scale unit. Referring to FIG. 1, a 90 mass % propane-5 mass % ethane-5 mass % hydrocarbons containing greater than three carbon atoms feedstock in line 2 and a recycle stream 22 of propane and hydrocarbons containing greater than three carbon atoms are introduced to a feed fractionation zone 4 operated at 66° C. and 225 psig to provide an overhead stream containing 97 mass % propane conducted in line 8 and a bottoms stream containing mainly hydrocarbons having greater than three carbon atoms conducted in line 6. The overhead stream containing 97 mass % propane conducted in line 8 is passed to dehydrogenation reaction zone 10 operated at 650° C. and 5 psig which contains a platinum containing catalyst.

In dehydrogenation reaction zone 10, a portion of the propane is dehydrogenated to form propylene. The effluent of dehydrogenation reaction zone 10 conducted in line 12 contains a mixture of propane, propylene, hydrogen, methane, ethane, ethylene, and hydrocarbons containing greater than three carbon atoms and is passed to separation zone 14. In separation zone 14, the effluent is cooled and separated into a hydrogen-rich vapor phase in line 16 and a hydrocarbon-rich liquid phase in line 18. A portion of the hydrogen-rich vapor phase in line 16 may be recycled to dehydrogenation reaction zone 10 via line 17. Separation zone 14 is operated at −120° C. and 125 psig. The hydrocarbon-rich liquid phase in line 18 is passed to a propane-propylene splitter 20 operated at 50° C. and 300 psig. In propane-propylene splitter 20 the hydrocarbon-rich liquid phase is separated into a propylene enriched stream containing 79 mass % propylene in line 24 and a propane enriched stream in line 22. Line 22 is recycled to combine with the feedstock in line 2. Line 24 is passed to diisopropyl ether reaction zone 26 which is operated at 150° C. and 1000 psig and contains sulfonated styrene/divinylbenzene co-polymer ion exchange resin catalyst. Lines 50 and 28 provide water to diisopropyl ether reaction zone 26.

In diisopropyl ether reaction zone 26, the hydrolysis of propylene is catalyzed and isopropyl alcohol is formed, concurrently the isopropyl alcohol is catalytically reacted with propylene to form diisopropyl ether. The diisopropyl ether reaction zone effluent 30 contains propylene, propane, water, isopropyl alcohol, and diisopropyl ether. A portion of effluent 30 is recycled to diisopropyl ether reaction zone 26 in line 32 and the remainder is passed in line 34 to a light ends removal zone 36. Fractionation in light ends removal zone 36 at 112° C. and 325 psig results in a methane, ethane, and ethylene stream in line 38, a propane and propylene stream 42 which is recycled to the propane-propylene splitter 20, and a water, isopropyl alcohol and diisopropyl ether stream 40 which is passed to a water-isopropyl alcohol-diisopropyl ether splitter column 44. In water-isopropyl alcohol-diisopropyl ether splitter column 44 the water, isopropyl alcohol and diisopropyl ether stream 40 is fractionated to form a water stream 46, a water-isopropyl alcohol azeotrope stream 50, and a diisopropyl ether-isopropyl alcohol-water azeotrope stream 48. Water-isopropyl alcohol azeotrope stream 50 is recycled to diisopropyl ether reaction zone 26, and water stream 46 is recycled to a water wash unit 58. Diisopropyl ether-isopropyl alcohol-water azeotrope stream 48 is passed to settler 52 where the azeotrope separates into a water rich stream 54 and a diisopropyl ether rich stream 56. Diisopropyl ether rich stream 56 is passed to water wash unit 58. A water feed 64 which is combined with water stream 46 from the water-isopropyl alcohol-diisopropyl ether splitter column 44 is also introduced to water wash unit 58. Isopropyl alcohol present in diisopropyl ether rich stream 56 is extracted into the water in water wash unit 58 and exits in water and isopropyl alcohol stream 60 which is combined with water rich stream 54 and recycled to water-isopropyl alcohol-diisopropyl ether splitter column 44. A diisopropyl ether product stream 62 containing at least 96 mass % diisopropyl ether is withdrawn from water wash unit 58 and collected.

Figure 2:
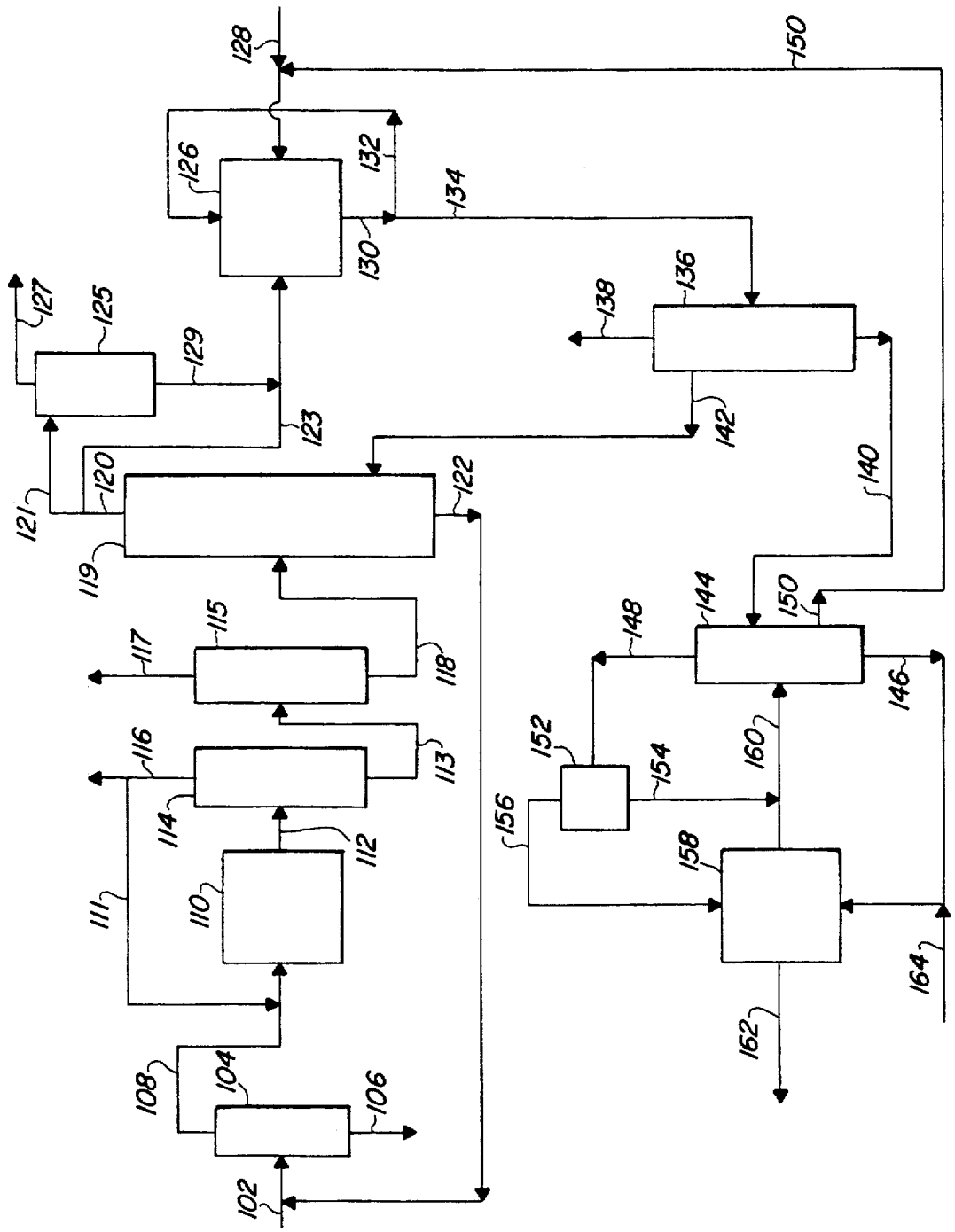
FIG. 2 is a schematic representation of a variant of the invention where high purity propylene is collected as product as well as diisopropyl ether.

The variant of the invention where high purity propylene is collected as product as well as diisopropyl ether is illustrated in FIG. 2. Referring to FIG. 2, a 90 mass % propane-5 mass % ethane-5 mass % hydrocarbons containing greater than three carbon atoms feedstock 102 and a recycle stream 122 of propane and hydrocarbons containing greater than three carbon atoms are introduced to a feed fractionation zone 104 operated at 66° C. and 225 psig to provide an overhead stream containing 97 mass % propane conducted in line 108 and a bottoms stream containing mainly hydrocarbons having greater than three carbon atoms conducted in line 106. The overhead stream containing 97 mass % propane conducted in line 108 is passed to dehydrogenation reaction zone 110 operated at 650° C. and 5 psig which contains platinum containing catalyst.

In dehydrogenation reaction zone 110 a portion of the propane is dehydrogenated to form propylene. The effluent of dehydrogenation reaction zone 110 conducted in line 112 contains a mixture of propane, propylene, hydrogen, methane, ethane, ethylene, and hydrocarbons containing greater than three carbon atoms and is passed to separation zone 114. In separation zone 114, the effluent is cooled and separated into a hydrogen-rich vapor phase in line 116 and a hydrocarbon-rich liquid phase in line 113. A portion of the hydrogen-rich vapor phase in line 116 may be recycled to dehydrogenation reaction zone 110 via line 111. Separation zone 114 is operated at −120° C. and 125 psig. Hydrocarbon-rich liquid phase in line 113 is passed to another separation zone 115 where methane, ethane, and ethylene are fractionated into line 117 and propane, propylene, and hydrocarbons containing greater than three carbons atoms are fractionated into line 118. Line 118 is introduced to a propane-propylene splitter 119 operated at 33° C. and 171 psig. In propane-propylene splitter 119 the hydrocarbon-rich liquid phase is separated into a propylene enriched stream containing 79 mass % propylene in line 120 and a propane enriched stream in line 122. Line 122 is recycled to combine with the feedstock in line 102. The propylene enriched stream containing 79 mass % propylene in line 120 is divided into two portions. Line 121 conducts the first portion to finishing column 125 and line 123 conducts the second portion to diisopropyl ether reaction zone 126. Finishing column 125 is a fractionation column operated at 33° C. and 171 psig to further separate propane and propylene and produce a propylene stream containing 99.5 mass % propylene in line 127 which is collected as high purity propylene product. Line 129 conducts the propane bottoms which contain about 1.5% propylene to combine with line 123.

Diisopropyl ether reaction zone 126 is operated at 150° C. and 1000 psig and contains sulfonated styrene/divinylbenzene co-polymer ion exchange resin catalyst. Lines 150 and 128 provide water to diisopropyl ether reaction zone 126. In diisopropyl ether reaction zone 126, the hydrolysis of propylene is catalyzed and isopropyl alcohol is formed, the isopropyl alcohol is then catalytically reacted with propylene to form diisopropyl ether. The diisopropyl ether reaction zone effluent 130 contains propylene, propane, water, isopropyl alcohol, and diisopropyl ether. A portion of the effluent 130 is recycled to diisopropyl ether reaction zone 126 in line 132 and the remainder is passed in line 134 to a light ends removal zone 136. Fractionation in light ends removal zone 136 at 80° C. and 235 psig results in a methane, ethane, ethylene stream in line 138, a propane and propylene stream in line 142 which is recycled to the propane-propylene splitter 119, and a water, isopropyl alcohol and diisopropyl ether stream in line 140 which is passed to a water-isopropyl alcohol-diisopropyl ether splitter column 144. In water-isopropyl alcohol-diisopropyl ether splitter column 144 the water, isopropyl alcohol and diisopropyl ether stream 134 is fractionated to form a water stream 146, a water-isopropyl alcohol azeotrope stream 150, and a diisopropyl ether-isopropyl alcohol-water azeotrope stream 148. Water-isopropyl alcohol azeotrope stream 150 is recycled to diisopropyl ether reaction zone 126, and water stream 146 is recycled to a water wash unit 158. Diisopropyl ether-isopropyl alcohol-water azeotrope stream 148 is passed to settler 152 where the azeotrope separates into a water rich stream 154 and a diisopropyl ether rich stream 156. Diisopropyl ether rich stream 156 is passed to water wash unit 158. A water feed 164 which is combined with water stream 146 from the water-isopropyl alcohol-diisopropyl ether splitter column 144 is also introduced to water wash unit 158. Isopropyl alcohol present in diisopropyl ether rich stream 156 is extracted into the water in water wash unit 158 and exits in water and isopropyl alcohol stream 160 which is combined with water rich stream 154 and recycled to water-isopropyl alcohol-diisopropyl ether splitter column 144. A diisopropyl ether product stream 162 containing at least 96 mass % diisopropyl ether is withdrawn from water wash unit 158 and collected.

What is claimed is:

1. A process for producing diisopropyl ether from propane in a feedstock containing at least 95 mass % propane and substantially depleted of hydrocarbons containing more than three carbon atoms, said process comprising:
   a) catalytically dehydrogenating the propane in a first reaction zone to produce propylene in a first reaction zone effluent;
   b) separating the propylene from the first reaction zone effluent in a first separation zone and catalytically reacting in a second reaction zone the separated propylene with water to produce isopropyl alcohol and diisopropyl ether in a second reaction zone effluent;
   c) separating, in a second separation zone, a propane and propylene mixture and a water, diisopropyl ether, and isopropyl alcohol mixture from the second reaction zone effluent;
   d) recycling the propane and propylene mixture to the first separation zone; and
   e) collecting the water, diisopropyl ether, and isopropyl alcohol mixture.

2. The process of claim 1 where separating the propylene from the first reaction zone effluent results in a separated propylene stream containing at least 65 mass % propylene.

3. The process of claim 1 further comprising recycling a portion of the second reaction zone effluent to the second reaction zone.

4. The process of claim 1 further comprising:
   a) separating in a third separation zone the water, diisopropyl ether, and isopropyl alcohol mixture into a diisopropyl ether enriched stream, an isopropyl alcohol and water enriched stream, and a water enriched stream;
   b) recycling the isopropyl alcohol and water enriched stream to the second reaction zone, and passing the water enriched stream to a water wash unit;
   c) water washing the diisopropyl ether enriched stream in the water wash unit to produce a diisopropyl ether product stream containing at least 96 mass % diisopropyl ether; and
   d) collecting the diisopropyl ether product stream.

5. A process for producing propylene and diisopropyl ether from propane in a feedstock containing at least 95 mass % propane and substantially depleted of hydrocarbons containing more than three carbon atoms, said process comprising:
   a) catalytically dehydrogenating the propane in a first reaction zone to produce a first reaction zone effluent containing propylene and hydrocarbons containing less than three carbon atoms;
   b) removing hydrocarbons containing less than three carbon atoms and separating, in a first separation zone, the propylene from the first reaction zone effluent;
   c) catalytically reacting, in a second reaction zone, a first portion of the separated propylene with water to produce isopropyl alcohol and diisopropyl ether in a second reaction zone effluent;
   d) subjecting a second portion of the separated propylene to further purification to afford a product stream containing at least 90 mass % propylene;
   e) separating, in a second separation zone, a propane and propylene mixture and a water, diisopropyl ether, and isopropyl alcohol mixture from the first portion of the second reaction zone effluent;
   f) recycling the propane and propylene mixture to the first separation zone; and
   g) collecting the water, diisopropyl ether, and isopropyl alcohol mixture, and the stream containing at least 90 mass % propylene.

6. The process of claim 5 further comprising recycling a portion of the second reaction zone effluent to the second reaction zone.

7. The process of claim 5 where the purification of step (d) is accomplished using fractionation.

8. The process of claim 5 further comprising:
   a) separating in a third separation zone the water, diisopropyl ether, and isopropyl alcohol mixture into a diisopropyl ether enriched stream, an isopropyl alcohol and water enriched stream, and a water enriched stream;
   b) recycling the isopropyl alcohol and water enriched stream to the second reaction zone and passing the water enriched stream to a water wash unit;
   c) water washing the diisopropyl ether enriched stream in the water wash unit to produce a diisopropyl ether product stream containing at least 96 mass % diisopropyl ether; and
   d) collecting the diisopropyl ether product stream.

9. A process for producing diisopropyl ether from propane in a feedstock containing at least 95 mass % propane and substantially depleted of hydrocarbons containing more than three carbon atoms, said process comprising:
   a) catalytically dehydrogenating the propane of the feedstock in a first reaction zone to produce a first reaction zone effluent containing hydrogen, propane, and propylene;
   b) removing hydrogen from the first reaction zone effluent to afford a hydrogen-depleted stream;
   c) separating, in a first separation zone, the hydrogen-depleted stream into a propane enriched stream and a propylene enriched stream, said propylene enriched stream containing at least 65 mass % propylene;
   d) catalytically reacting, in a second reaction zone, water and the propylene of the propylene enriched stream to produce isopropyl alcohol and diisopropyl ether in a second reaction zone effluent;
   e) recycling a portion of the second reaction zone effluent to the second reaction zone;
   f) separating, in a second separation zone, the remainder of the second reaction zone effluent into a light ends-depleted stream, a propane and propylene enriched stream, and a light ends enriched stream;
   g) recycling the propane and propylene enriched stream to the first separation zone;
   h) separating, in a third separation zone, the light ends-depleted stream into a diisopropyl ether enriched stream, an isopropyl alcohol and water enriched stream, and a water enriched stream, recycling the isopropyl alcohol and water enriched stream to the second reaction zone, and passing the water enriched stream to a water wash unit;
   i) water washing the diisopropyl ether enriched stream in the water wash unit to produce a diisopropyl ether product stream containing at least 96 mass % diisopropyl ether; and j) collecting the diisopropyl ether product stream.

10. The process of claim 9 further comprising where the feedstock contains ethane, a portion of which is dehydrogenated in step (a), and the product ethylene is reacted in step (d) to produce isopropyl ethyl ether in the second reaction zone effluent.

11. A process for producing diisopropyl ether from propane in a feedstock containing at least 95 mass % propane and substantially depleted of hydrocarbons containing more than three carbon atoms, said process comprising:

a) catalytically dehydrogenating the propane of the feedstock in a first reaction zone to produce a first reaction zone effluent containing hydrogen, propane, propylene, and hydrocarbons containing less than three carbon atoms;

b) removing the hydrogen and hydrocarbons containing less than three carbon atoms from the first reaction zone effluent to afford a largely propane and propylene stream;

c) separating, in a first separation zone, the largely propane and propylene stream into a propane enriched stream and a propylene enriched stream, said propylene enriched stream containing at least 65 mass % propylene;

d) further separating, in a second separation zone, a portion of the propylene enriched stream into a high purity propylene product stream containing at least 90 mass % propylene, and a low purity propylene stream, and recycling the low purity propylene stream to the first separation zone;

e) catalytically reacting, in a second reaction zone, water and the propylene of the remainder of the propylene enriched steam to produce isopropyl alcohol and diisopropyl ether in a second reaction zone effluent;

f) recycling a portion of the second reaction zone effluent to the second reaction zone;

g) separating, in a third separation zone, the remainder of the second reaction zone effluent into a light ends-depleted stream, a propane and propylene enriched stream, and a light ends enriched stream;

h) recycling the propane and propylene enriched stream to the first separation zone;

i) separating, in a fourth separation zone, the light ends-depleted stream into a diisopropyl ether enriched stream, an isopropyl alcohol and water enriched stream, and a water enriched stream, recycling the isopropyl alcohol and water enriched stream to the second reaction zone, and passing the water enriched stream to a water wash unit;

j) water washing the diisopropyl ether enriched stream in the water wash unit to produce a diisopropyl ether product stream containing at least 96 mass % diisopropyl ether; and k) collecting the diisopropyl ether product stream.

* * * * *